US006315907B1

(12) United States Patent
Hirai et al.

(10) Patent No.: US 6,315,907 B1
(45) Date of Patent: Nov. 13, 2001

(54) METHOD FOR REMOVING TOXIC SHOCK SYNDROME TOXIN-1 IN BODY FLUIDS BY ADSORPTION

(75) Inventors: Fumiyasu Hirai, Amagasaki; Eiji Ogino, Kobe; Hiroyuki Maruyama, Kakogawa; Takayuki Sakogawa, Takasago; Takashi Asahi, Kobe; Nobutaka Tani, Osaka, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/403,281
(22) PCT Filed: Apr. 13, 1998
(86) PCT No.: PCT/JP98/01704
§ 371 Date: Oct. 19, 1999
§ 102(e) Date: Oct. 19, 1999
(87) PCT Pub. No.: WO98/47548
PCT Pub. Date: Oct. 29, 1998

(30) Foreign Application Priority Data

Apr. 21, 1997 (JP) .................................... 9-103576

(51) Int. Cl.[7] .................................................. B01D 15/00
(52) U.S. Cl. .......................................... 210/679; 210/691
(58) Field of Search ............................... 210/679, 690, 210/691, 263, 502.1, 506; 502/401

(56) References Cited

U.S. PATENT DOCUMENTS 4,814,077 * 3/1989 Furuyoshi et al. ................. 210/502.1
5,279,821 * 1/1994 Hirayama et al. ................... 210/679
5,919,898   7/1999 Nakatani et al. ..................... 530/345

FOREIGN PATENT DOCUMENTS 0 247 592 A2   12/1987   (EP) .
0 723 794 A1    7/1996   (EP) .
0 743 067 A2   11/1996   (EP) .
  5-253479     10/1993   (JP) .

OTHER PUBLICATIONS

Patric M. et al., "Identification and Characterization of an Exotoxin from *Stafpylococcus aureus* Associated with Toxic–shock Syndrome,", *The Journal of Infection Diseases*, vol. 143 (No. 4), pp. 509–516 (1981).
Igarashi H. et al., "Purification and Characterization of *Stafpylococcus aureus* FRI1169 and 587 Toxic Shock Syndrome Exotoxins", *Infection and Immunity*, vol. 44 (No. 1), pp. 175–181 (1984).
European Search Report dated Feb. 4, 2000.

* cited by examiner

*Primary Examiner*—Ivars Cintins
(74) *Attorney, Agent, or Firm*—Armstrong, Westerman, Hattori, McLeland & Naughton, LLP

(57) ABSTRACT

An adsorbent for toxic shock syndrome toxin-1 (TSST-1) comprising a compound which has a log P value of at least 2.50 wherein P is a partition coefficient in an octanol-water system and which is immobilized on a water-insoluble carrier; a method for removing TSST-1 body fluids by adsorption which comprises bringing a body fluid containing TSST-1 into contact with the adsorbent; an adsorber for TSST-1 comprising an adsorbent packed in a container having an inlet and an outlet for a body fluid and a means for preventing the adsorbent from flowing out of the container; and use of the adsorbent. TSST-1 in body fluids can be efficiently removed by the adsorbent.

12 Claims, 2 Drawing Sheets

METHOD FOR REMOVING TOXIC SHOCK SYNDROME TOXIN-1 IN BODY FLUIDS BY ADSORPTION

TECHNICAL FIELD

The present invention relates to an adsorbent for toxic shock syndrome toxin 1, a method for removing the toxin by adsorption, an adsorber comprising the adsorbent packed, and use of the adsorbent.

BACKGROUND ART

The toxic shock syndrome toxin 1 (hereinafter referred to as "TSST-1") is an exotoxin composed of a soluble protein having a molecular weight of about 20–30 kDa produced by *Staphylococcus aureus*, and is a representative superantigen.

Sepsis refers to a state that an infection exists somewhere in a body, whereby a systemic inflammatory response has occurred. If this inflammatory symptom accelerates, a shock symptom (septic shock) occurs, and organopathy (organ failure) occurs, further falling into such a grave state as multi-organ failures. The source of that infection is mainly bacteria, and the bacteria is roughly classified into Gram-positive bacteria and Gram-negative bacteria.

If infected with *Staphylococcus aureus* which is a sort of Gram-positive bacteria, TSST-1 produced by the infecting *Staphylococcus aureus* propagates and activates T-cells to cause sepsis. Recently, infection with methicillin resistant *Staphylococcus aureus* (MRSA) and septic shock accompanied thereby attract attention as an important prophlogistic bacteria of nosocomial infection and have come a large social problem for the last several years (Tomoyuki Kawamata et al., Intensive & Critical Care Medicine, Vol. 7, page 631, 1995).

On the other hand, if infected with Gram-negative bacteria, endotoxin present in the cell wall of the bacteria enters into blood to cause sepsis. Further, in recent years, it is reported that since TSST-1 activates immune system as a superantigen to enhance the toxicity of endotoxin to several thousands times, sepsis is caused even by the presence of such a low concentration of endotoxin that cannot clinically cause sepsis. Thus, in case of mixed infection with both Gram-positive bacteria and Gram-negative bacteria, a possibility of causing sepsis becomes very high.

Antibiotics as a countermeasure for infection and γ-globulin to activate the resistance to infection have been used for the treatment of sepsis, but the mortality is still high. For the reason, it has been desired from the medical point of view to remove TSST-1 and endotoxin which become a cause of sepsis from body fluids.

As to endotoxin, adsorbents to remove it from body fluids are known. For example, Japanese Patent Publication Kokoku No. 1-16389 discloses an adsorbent wherein polymyxin known as an antidote to endotoxin is immobilized on a suitable carrier. Also, the present inventors disclose in Japanese Patent Publication Kokai No. 8-173803 that endotoxin can be adsorbed by a sulfo group-introduced styrene-divinyl benzene copolymer. These adsorbents are expected to produce a fairly large effect against infection with Gram-negative bacteria. However, in case that both TSST-1 and endotoxin coexist as a result of mixed infection with Gram-positive bacteria and Gram-negative bacteria, the effect lowers. Further, in case that a person is infected with only Gram-positive bacteria and TSST-1 enters a body fluid, no effect is expected. Various adsorbents for endotoxin are known, but no adsorbent for TSST-1 has been known. Thus, development of adsorbent for TSST-1 has been strongly desired.

An object of the present invention is to provide an adsorbent capable of efficiently removing TSST-1 present in body fluids, a method and an adsorber for removing TSST-1 in body fluids by adsorption with the adsorbent, and use of the adsorbent.

DISCLOSURE OF INVENTION

The present inventors made an intensive study on adsorbents capable of efficiently removing TSST-1 present in body fluids. As a result, the present inventors have found that an adsorbent comprising a water-insoluble carrier and a compound having a log P value of at least 2.50 immobilized on the carrier can efficiently adsorb and remove TSST-1 present in body fluids, thus they have accomplished the present invention.

That is to say, the present invention relates to (1) an adsorbent for TSST-1 comprising a water-insoble carrier and a compound having a log P value of at least 2.50 wherein P is a partition coefficient in an octanol-water system, the compound being immobilized on the carrier.

Further, the present invention relates to (2) the adsorbent mentioned in (1), wherein the water-insoluble carrier is a water-insoluble porous carrier.

Further, the present invention relates to (3) the adsorbent mentioned in (2), wherein the water-insoluble carrier has an exclusion limit for globular protein of from $1 \times 10^4$ to $60 \times 10^4$.

Further, the present invention relates to (4) a method for removing TSST-1 in body fluid, characterized by bringing a body fluid containing TSST-1 into contact with the adsorbent mentioned in (1).

Further, the present invention relates to (5) an adsorber for TSST-1 comprising a container having an inlet and an outlet for a body fluid and a means for preventing an adsorbent from flowing out of the container, and the adsorbent mentioned in (1) which is packed in the container.

Further, the present invention relates to (6) use of an adsorbent comprising a water-insoluble carrier and a compound having a log P value of at least 2.50 and immobilized on the carrier, wherein P is a partition coefficient in an octanol-water system, for the manufacture of an adsorbent for toxic shock syndrome toxin-1.

BEST MODE FOR CARRING OUT THE INVENTION

Figure 1:
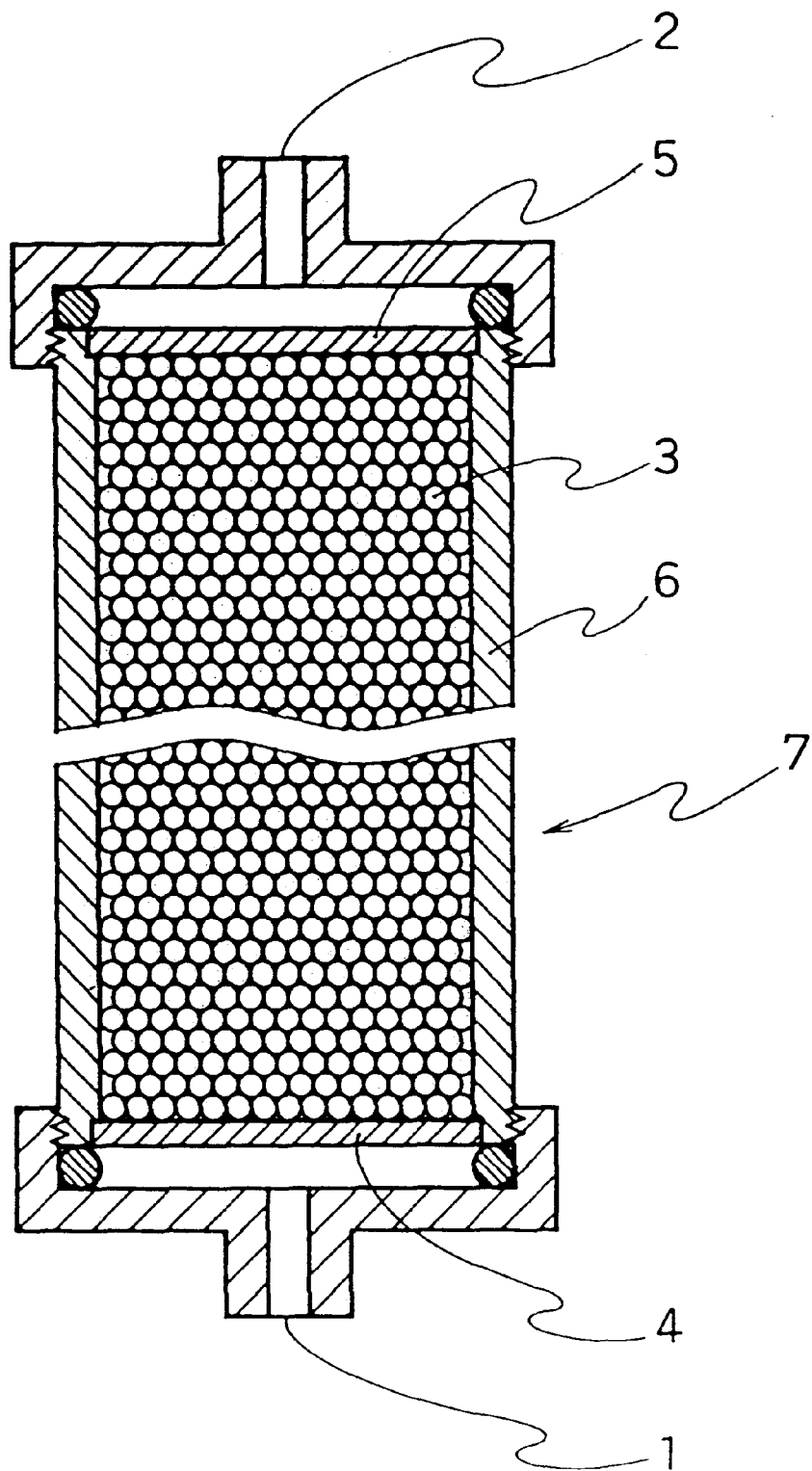
FIG. 1 is a schematic cross section view showing an example of an adsorber for TSST-1 according to the present invention.
Figure 2:
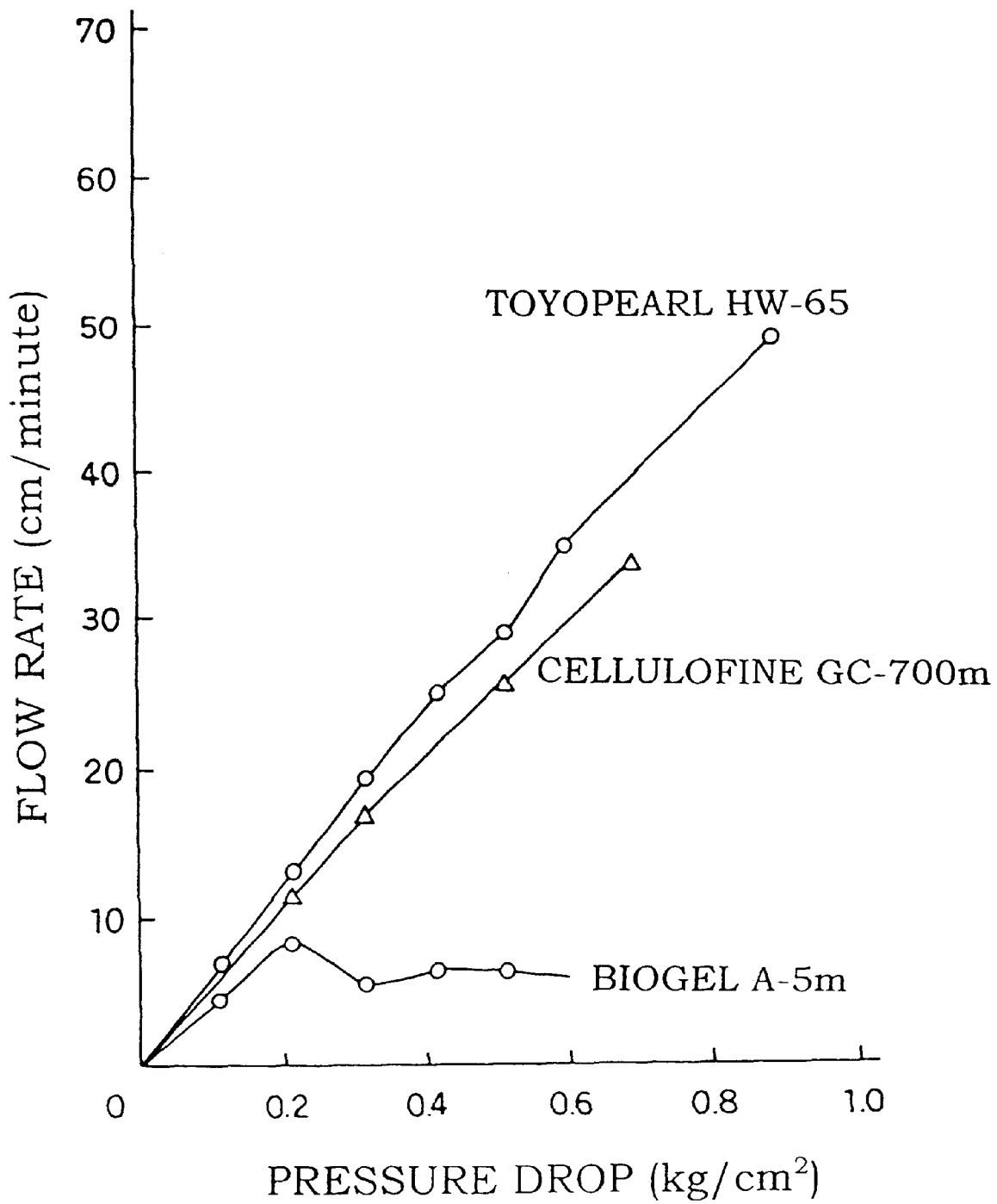
FIG. 2 is a graph showing results of examining a relationship between the flow rate and the pressure drop AP by using three kinds of water-insoluble carriers.

The "TSST-1" in the present invention is an exotoxin composed of a soluble protein having a molecular weight of about 20–30 kDa produced by Staphylococcus aureus.

Also, the body fluid means blood, plasma, serum, ascites, lymph, synovia and fractions obtained from them, and other liquid components derived from a living body.

The log P value is a parameter which indicates the hydrophobicity of a compound. A typical partition coefficient P in an octanol-water system is determined as follows: At first, a compound is dissolved in octanol (or water) and an equal amount of water (or octanol) is added thereto. After shaking the mixture for 30 minutes with a Griffin flask shaker (made by Griffin & George Ltd.), the mixture is centrifuged for 1 to 2 hours at 2,000 r.p.m. The respective concentrations of the compound in both octanol and water layers are measured by various methods such as spectroscopic method or GLC, and the partition coefficient P is obtained from the following equation.

$$P = C_{oct}/C_w$$

$C_{oct}$: concentration of a compound in the octanol layer
$C_w$: concentration of a compound in the water layer The adsorbent of the present invention comprises a compound, the logarithmic value of P as obtained in the above manner (log P value) of which is 2.50 or more, and which is immobilized on a water-insoluble carrier.

Until now, many investigators have determined log P values of various compounds and the found values of the log P are put in order by C. Hansch et al ("PARTITION COEFFICIENTS AND THEIR USES"; Chemical Reviews, 71, page 525 (1971)).

As to compounds whose found values are unknown, calculated values ($\Sigma f$) obtained by using a hydrophobic fragmental constant f shown in R. F. Rekker's book ("THE HYDROPHOBIC FRAGMENTAL CONSTANT", Elsevier Sci. Pub. Corn., Amsterdam, 1977) can be a good guide. The hydrophobic fragmental constant f is a value showing the hydrophobicity of various fragments determined by a statistical treatment of many found values of log P. The sum of f values of respective fragments which constitute a compound approximately agree with log P of the compound. In the present invention, the log P value of a compound means $\Sigma f$ value when the log P value of the compound is not known.

In investigating compounds effective for adsorbing TSST-1, compounds having various log P values were immobilized on a water-insoluble carrier and the adsorption ability thereof were examined with respect to TSST-1. As a result, it has been found that compounds having a log P value of 2.50 or more, preferably 2.80 or more, more preferably 3.00 or more, are effective for adsorption of TSST-1, and that compounds having a log P value of less than 2.5 hardly show an adsorption ability for TSST-1. For example, in the case of immobilizing an alkylamine on a water-insoluble carrier, it has been found that the absorption ability for TSST-1 is enhanced to a great extent when the alkylamine is changed from n-hexylamine (log P=2.06)) to n-octylamine (log P=2.90). From these results, it is assumed that the adsorption ability of the adsorbent according to the present invention with respect to TSST-1 is based on a hydrophobic interaction between TSST-1 and an atomic group introduced onto a carrier by immobilization of a compound having a log p value of 2.50 or more, and that a compound having a log P value of less than 2.50 does not show any ability for adsorbing TSST-1 because the hydrophobicity of this compound is too low.

In the present invention, compounds to be immobilized onto a water-insoluble carrier can be employed without particular limitation so long as they have a log P value of 2.50 or more. However, in case of immobilizing a compound onto a carrier by a chemical bonding method, a part of the compound is often eliminated. When the eliminated group greatly contributes to the hydrophobicity of the compound, that is to say, when the hydrophobicity of an atomic group immobilized onto the carrier becomes smaller than Σf=2.50 due to the elimination, such a compound is not suitable as the compound to be used in the present invention from the viewpoint of the gist of the present invention. A typical example thereof is a case where isopentyl benzoate (Σf=4.15) is immobilized onto a carrier having hydroxyl group by transesterification. In this case, the atomic group which is actually immobilized onto the carrier is $C_6H_5$—CO—, the Σf value of which is 1 or less. Whether such compounds are suitable or not as a compound used in the present invention may be judged by determining whether the log P value of a compound obtainable by substituting the eliminating part by hydrogen is not less than 2.50 or not.

Among compounds having a log P value of 2.50 or more, preferable are compounds having a functional group which can be utilized for binding the compound to a carrier, e.g., unsaturated hydrocarbons, alcohols, amines, thiols, carboxylic acids and derivatives thereof, halides, aldehydes, hydrazids, isocyanates, compounds containing an oxirane ring such as glycidyl ethers, and halogenated silanes. Typical examples of these compounds are, for instance, amines such as n-heptylamine, n-octylamine, decylamine, dodecylamine, hexadecylamine, octadecylamine, 2-aminooctene, naphthylamine, phenyl-n-propylamine, diphenylmethylamine, and the like; alcohols such as n-heptyl alcohol, n-octyl alcohol, dodecyl alcohol, hexadecyl alcohol, 1-octene-3-ol, naphthol, diphenylmethanol, 4-phenyl-2-butanol, and the like, and glycidyl ethers of these alcohols; carboxylic acids such as n-octanoic acid, nonanoic acid, 2-nonenoic acid, decanoic acid, dodecanoic acid, stearic acid, arachidonic acid, oleic acid, diphenylacetic acid, phenylpropionic acid, and the like, and their acid halides; carboxylic acid derivatives such as esters and amides; halides such as octyl chloride, octyl bromide, decyl chloride, dodecyl chloride, and the like; thiols such as octanethiol, dodecanethiol, and the like; halogenated silanes such as n-octyltrichlorosilane, octadecyltrichlorosilane, and the like; and aldehydes such as n-octylaldehyde, n-caprinaldehyde, dodecylaldehyde, and the like.

Besides, there can be used other compounds, e.g., compounds having a log P value of 2.5 or more selected from compounds in which a substituent containing a heteroatom such as halogen, nitrogen, oxygen or sulfur, or other alkyl group, is substituted for hydrogen atom contained in the hydrocarbon moiety of the above-exemplified compounds; and compounds having a log P value of 2.5 or more shown in the above-mentioned review by C. Hansch et al, "PARTITION COEFFICIENTS AND THEIR USES", Chemical Reviews, vol. 71, 525(1971), tables on pages 555 to 613. However, compounds which can be used in the present invention are not limited to these compounds only.

These compounds may be used alone or in an arbitrary combination thereof. Further, these compounds may be used in combination with a compound having a log P value of less than 2.5.

The "water-insoluble carrier" in the adsorbent of the present invention means a carrier which is solid at ordinary temperature under ordinary pressure and is insoluble in water.

The water-insoluble carrier in the present invention may be in the form of, for example, particle, board, fiber, hollow fiber, and the like, but the form thereof is not limited thereto. The size of the carrier is not also particularly limited.

Typical examples of the water-insoluble carrier in the present invention are, for instance, inorganic carriers such as glass beads and silica gel, organic carriers each comprising synthetic polymers such as crosslinked or non-crosslinked polyvinyl alcohol, crosslinked or non-crosslinked polyacrylate, crosslinked or non-crosslinked polyacrylamide and crosslinked or non-crosslinked polystyrene, or polysaccharides such as crystalline celluloses, crosslinked or non-crosslinked celluloses, crosslinked or non-crosslinked agarose and crosslinked or non-crosslinked dextrin, and composite carriers each comprising a combination of the above-mentioned materials such as organic-organic carriers and organic-inorganic carriers.

Among these carriers, hydrophilic carriers are preferable since non-specific adsorption is comparatively a little and the adsorption selectivity for TSST-1 is good. The term "hydrophilic carrier" as herein used refers to a carrier composed of a material which has a contact angle with water of 60 degrees or less when the material is shaped into a flat plate. Typical examples of such hydrophilic carriers are, for instance, hose comprising cellulose, polyvinyl alcohol, hydrolyzed ethylene-vinyl acetate copolymer, polyacrylamide, polyacrylic acid, polymethacrylic acid, polymethyl methacrylate, polyacrylic acid-grafting polyethylene, polyacrylamide-grafting polyethylene, glass, and the like.

Of these, a porous cellulose gel is one of the most suitable carriers, since it has the superior properties that (1) the gel is hard to be destroyed or to become fine powder by an operation such as agitation because it has a comparatively high mechanical strength and toughness, so when the gel is packed in a column, compaction and choking of the column do not occur even if a body fluid is flowed at a high flow rate, and further the porous structure of the gel is hard to receive a change by a high pressure steam sterilization or the like, (2) since the gel is made of a cellulose, the gel is hydrophilic, and many hydroxyl group which can be utilized for bonding a ligand are present, and non-specific adsorption hardly occurs, (3) the adsorption capacity which is comparable to a soft gel can be obtained because the gel has a comparatively high strength even if the pore volume is made large, and (4) the safety is higher than synthetic polymer gels and the like. The carrier used in the present invention is preferably a hard gel that the flow rate does not increase in proportion to increase of the pressure, but is not limited thereto. The above-mentioned carriers may be used alone or in admixture thereof.

The property required for the water-insoluble carrier used in the present invention is to have a large number of pores having an adequate size, namely to be porous. TSST-1 which is the subject of adsorption by the adsorbent of the present invention is a protein having a molecular weight of about 20–30 kDa. It is preferable for efficiently adsorbing this protein that TSST-1 can enter the fine pores at some large probability but other proteins enter the pores as little as possible. Exclusion limit has been generally used as a measure of the molecular weight of a substance which can enter fine pores. The term "exclusion limit" means the molecular weight of the smallest molecule of molecules which cannot enter fine pores (namely which are excluded) in a gel permeation chromatography, as described in books (see, for example, Hiroyuki Hatano and Toshihiko Hanai, "Experimental High Performance Liquid Chromatography", Kagaku Dojin). In general, the exclusion limit has been well examined with use of globular protein, dextran, polyethlene glycol or the like. In the case of the water-insoluble porous carrier used in the present invention, it is suitable to use the values obtained by using globular protein.

As a result of study using carriers of various exclusion limits, it has become clear that the range of exclusion limit suitable for adsorbing TSST-1 is from $1\times10^4$ to $60\times10^4$. That is to say, when a carrier having an exclusion limit of less than $1\times10^4$ is used, the amount of TSST-1 adsorbed is small, so the practicability becomes low. When a carrier having an exclusion limit of more than $60\times10^4$ is used, proteins (mainly albumin) other than TSST-1 are adsorbed in an increased amount, so the practicability is low from the viewpoint of selectivity. Accordingly, the exclusion limit of the carrier used in the present invention is preferably from $1\times10^4$ to $60\times10^4$, more preferably from $1.5\times10^4$ to $40\times10^4$, further preferably from $2\times10^4$ to $30\times10^4$.

As to the pore structure of carriers, it is preferable from the viewpoint of the adsorption ability per unit volume of an adsorbent that the carrier is porous throughout the entire thereof rather than being porous only in the surface region. Preferably, the pore volume is at least 20% and the specific surface area is at least 3 $m^2/g$.

Further it is preferable that the carrier has a functional group which can be used in a reaction for immobilizing a ligand to the carrier. Typical examples of the functional group are, for instance, hydroxyl group, amino group, aldehyde group, carboxyl group, thiol group, silanol group, amide group, epoxy group, halogen, succinimide group, acid anhydride group, and the like. The functional groups are not limited to the exemplified groups.

Any of a hard carrier and a soft carrier can be used as the water-insoluble carrier in the present invention. In the case of using an adsorbent for an extracorporeal circulation, it is important that the adsorbent does not clog up when it is charged in a column and a fluid is flowed through the column. For this purpose, a sufficient mechanical strength is required for the adsorbent. Accordingly it is more preferable to use a hard carrier as the water-insoluble carrier in the present invention. The term "hard carrier" as used herein refers to, for example, in the case of a granulated gel, a carrier which has such a property that a linear relation between pressure drop $\Delta P$ and flow rate is held up to a pressure drop of 0.3 $kg/cm^2$ when the gel is uniformly charged in a cylindrical column and an aqueous fluid is passed through it, as shown in Reference Example described after.

The adsorbent of the present invention is obtained by immobilizing a compound having a log P value of 2.50 or more on a water-insoluble carrier. Various known methods of immobilization can be used without particular restriction. However, when the adsorbent of the present invention is used for an extracorporeal circulation treatment, it is important from the viewpoint of safety to suppress the elimination or elution of a ligand as much as possible in sterilization or treatment. For this purpose, preferably the immobilization is conducted by a covalent bond method.

In the adsorbent of the present invention, it is preferable that a proper amount of a compound having a log P value of 2.50 or more is immobilized. If the amount of the compound immobilized is too small, TSST-1 is not adsorbed. If the a mount is too large, a sticky component such as platelets may adhere to the adsorbent when blood is used as a body fluid. Thus, the amount of a compound having a log P value of at least 2.50 to be immobilized is preferably from 0.1 to 10,000 $\mu$mol, more preferably from 1 to 200 $\mu$mol, the most preferably from 5 to 100 $\mu$mol, per unit volume (1 ml) of a water-insoluble carrier.

Various methods are adoptable for adsorbing and removing TSST-1 from a body fluid by using the adsorbent of the present invention. The most simple method is a method wherein a body fluid is taken out and placed in a bag or the like and the adsorbent is mixed therewith to allow to adsorb TSST-1 and then the adsorbent is filtered off to obtain the body fluid from which TSST-1 has been removed. Another method is a method wherein the adsorbent is packed in a container which has an inlet and an outlet for a body fluid and which is equipped at least at the outlet with a filter which can pass a body fluid but cannot pass the adsorbent, and the body fluid is passed through the container. Both met hods can be used, but the latter method is adequate for the adsorbent of the present invention, since the operation is simple and TSST-1 can be removed efficiently in on-line system from a body fluid, especially blood, of a patient by incorporating the method into an extracorporeal circulation circuit. In the extracorporeal circulation circuit, the adsorbent of the present invention can be used not only singly but also in combination with other extracorporeal circulation therapy systems. As an example of the combination use is mentioned, for instance, an artificial dialysis circuit, and the adsorbent can be used in a combination with dialysis therapy.

An adsorber for TSST-1 of the present invention using the TSST-1 adsorbent mentioned above will be explained below with reference to FIG. 1 which is a schematic section view showing an example of the adsorber. In FIG. 1, 1 denotes an inlet for a body fluid, 2 denotes an outlet for the body fluid, 3 denotes the TSST-1 adsorbent of the present invention, 4 and 5 denote a filter (filter for preventing the adsorbent from flowing out) which can pass a body fluid and components included therein but cannot pass the adsorbent, 6 denotes a column, and 7 denotes an adsorber for TSST-1. The TSST-1 adsorber of the present invention is not limited to such an exemplified adsorber, and any devices can be adapted so long as the devices have a structure that the adsorbent mentioned before is packed in a container having an inlet and an outlet for a body fluid and equipped with a means for preventing the adsorbent from flowing out of the container.

Examples of the means for preventing the adsorbent from flowing out are, for instance, filters such as mesh, nonwoven fabric and cotton stopper. There is no particular limitation in the shape, material and size of the container, but a preferable example of the container is a transparent or semitransparent cylindrical container which, for instance, has a capacity of about 150 to about 400 ml and a diameter of about 4 to about 10 cm. Particularly preferable materials are those having a sterilization-resistance. Typical examples of such materials are, for instance, glass coated with a silicone, polypropylene, polyvinyl chloride, polycarbonate, polysulfone, polymethylpentene, and the like.

The present invention is explained below in more detail by means of Examples, but it is to be understood that the invention is not limited to only these Examples.

REFERENCE EXAMPLE

Cylindrical glass columns (inner diameter 9 mm, length 150 mm) equipped with filters having a pore size of 15 $\mu$m at both ends, were charged uniformly with each of an agarose gel (Biogel A-5m made by Bio-Rad Laboratories, U.S.A., particle size 50 to 100 meshes), a vinyl polymer gel (TOYOPEARL HW-65 made by TOSOH Corporation, Japan, particle size 50 to 100 $\mu$m) and a cellulose gel (CELLULOFINE GC-700m made by Chisso Corporation, Japan, particle size 45 to 105 $\mu$m). The relationship between flow rate and pressure drop $\Delta P$ was determined by passing water through the column with a peristatic pump. The results are shown in FIG. 2.

In FIG. 2, it is found that TOYOPEARL HW-65 and CELLULOFINE GC-700 m show that the flow rate increases almost in proportion to an increase in pressure, whereas Biogel A-5m causes a compaction and the flow rate does not increase even if the pressure is increased. In the present invention, a gel showing that the relationship between the pressure drop $\Delta P$ and the flow rate is linear up to a pressure drop of 0.3 kg/cm$^2$, like the former, is referred to as a hard gel.

Example 1

Water was added to 170 ml of a porous cellulose gel CELLULOFINE GC-200m (made by Chisso Corporation, Japan, exclusion limit for a globular protein 140,000) up to the total amount of 340 ml, and thereto was added 90 ml of a 2M aqueous solution of sodium hydroxide, and the mixture was kept at 40° C. To the mixture was then added 31 ml of epichlorohydrin, and the reaction was carried out with stirring at 40° C. for 2 hours. After the completion of the reaction, the gel was thoroughly washed with water to give an epoxidized gel.

To 10 ml of the epoxidized gel was added 200 mg of n-octylamine (log P=2.90), and the mixture was allowed to stand for ;reaction in a 50 v/v % aqueous solution of ethanol at 45° C. for 6 days to immobilize. After the completion of the reaction, the gel was thoroughly washed with a 50 v/v % aqueous ethanol solution, ethanol, a 50 v/v % aqueous ethanol solution and water in that order to give a n-octylamine-immobilized gel.

To 0.2 ml of the immobilized gel (adsorbent) was added 1.2 ml of a TSST-1-containing serum (TSST-1 concentration 5 ng/ ml) prepared by adding TSST-1 (made by Toxin Technology Corporation, U.S.A.) to a fetal calf serum (made by Flow Laboratories, Australia). The resulting mixture was incubated at 37° C. for 2 hours. The same procedure was conducted also with respect to 0.2 ml of physiological saline used instead of the adsorbent. Concentrations of TSST-1 in the supernatant before and after the incubation were measured by an ELISA method, and the adsorption rate was calculated by dividing the concentration in the supernatant obtained with the use of the adsorbent by the concentration in the supernatant obtained with the use of physiological saline (percentage).

The ELISA method for TSST-1 was conducted as follows: A primary antibody Rabbit Anti-TSST-1 IgG (made by Toxin Technology Corporation, U.S.A.) was diluted with a coating buffer to 1,600 times, and 100 $\mu$l portions thereof were distributed onto a microplate. After allowing to stand overnight at 4° C., the microplate was washed, and 200 $\mu$l portions of a 3% solution of bovine serum albumin were distributed onto the microplate. After allowing to stand at room temperature for 2 hours, the microplate was washed, and 100 $\mu$l of each of a TSST-1 standard liquid and the supernatants before and after incubation was added to the microplate. After allowing to stand at room temperature for 2 hours, the microplate was washed. A secondary antibody Rabbit Anti-TSST-1 HRPO (made by Toxin Technology Corporation, U.S.A.) was diluted with a 1% solution of bovine serum albumin to 400 times, and 100 $\mu$l portions thereof were distributed onto the microplate. After allowing to stand at room temperature for 2 hours, the microplate was washed. Thereto were distributed 100 $\mu$l portions of an o-phenylenediamine solution, and the microplate was allowed to stand at room temperature for 10 minutes. To the microplate were distributed 100 $\mu$l portions of 4N sulfuric acid and the absorbance was measured at 492 nm. The concentrations of TSST-1 in the supernatants before and after incubation was obtained by comparison with the absorbance of the standard liquid.

Example 2

A cetylamine-immobilized gel was prepared in the same manner as in Example 1 except that cetylamine (Σf=7.22) was used instead of n-octylamine (log P=2.90) and ethanol was used as a solvent for the immobilization reaction. Adsorption test was made in the same manner as in Example 1 by using this adsorbent, and the concentration of TSST-1 was measured and the adsorption rate was calculated.

Example 3

A cetylamine-immobilized gel was prepared in the same manner as in Example 1 except that CELLULOFINE GC-700m (made by Chisso Corporation, Japan, exclusion limit for a globular protein 400,000) was used instead of CELLULOFINE GC-200m. Adsorption test was made in the same manner as in Example 1 by using this adsorbent, and the concentration of TSST-1 was measured and the adsorption rate was calculated.

Example 4

To 10 ml of CELLULOFINE GC-200 m were added 10 ml of t-butyl alcohol and 2.0 g of potassium butoxide, and the resulting mixture was stirred at 40° C. for 1 hour. Then 2.0 ml of cetyl bromide (Σf=9.71 after immobilization) was added to the mixture and stirred for 4 hours. After the reaction, the gel was filtered off and washed with ethanol and water to give a cellulose gel onto which cetyl group is bound by ether bond. Adsorption test was made in the same manner as in Example 1 by using this adsorbent, and the concentration of TSST-1 was measured and the adsorption rate was calculated.

Comparative Example 1

A n-butylamine-immobilized gel was prepared in the same manner as in Example 1 except that n-butylamine (log P=0.97) was used instead of n-octylamine (log P=2.90). Adsorption test was made in the same manner as in Example 1 by using this adsorbent, and the concentration of TSST-1 was measured and the adsorption rate was calculated.

Comparative Example 2

A n-hexylamine-immobilized gel was prepared in the same manner as in Example 1 except that n-hexylamine (log P=2.06) was used instead of n-octylamine (log P=2.90). Adsorption test was made in the same manner as in Example 1 by using this adsorbent, and the concentration of TSST-1 was measured and the adsorption rate was calculated.

Log P values or Σf values of the compounds used in the Examples and Comparative Examples and the adsorption rate (%) calculated are shown in Table 1.

TABLE 1

| | log P (Σf) value | Adsorption rate (%) |
|---|---|---|
| Example 1 | 2.90 | 38 |
| Example 2 | 7.22 | 79 |
| Example 3 | 7.22 | 78 |
| Example 4 | 9.71 | 85 |
| Com. Ex. 1 | 0.97 | 4 |
| Com. Ex. 2 | 2.06 | 1 |

INDUSTRIAL APPLICABILITY

According to the present invention, TSST-1 in body fluids can be efficiently removed by using an adsorbent comprising a compound having a log P value of at least 2.50 immobilized on a water-insoluble carrier.

What is claimed is:

1. A method for removing toxic shock syndrome toxin-1 in body fluids which comprises bringing a body fluid containing toxic shock syndrome toxin-1 into contact with an absorbent comprising a water-insoluble carrier and a compound having a log P value of at least 2.50 wherein P is a partition coefficient in an octanol-water system wherein said compound is immobilized on said carrier.

2. The method of claim 1, wherein said water-soluble carrier is a water-soluble porous carrier.

3. The method of claim 1, wherein said water-insoluble carrier has an exclusion limit for globular protein of 10,000 to 600,000.

4. The method of claim 1, wherein said compound is covalently bonded to said carrier, and the total of hydrophobic fragmental constants f of fragments of said compound bonded to said carrier is not less than 2.50.

5. The method of claim 1, wherein said compound is an alkylamine.

6. The method of claim 5, wherein said alkylamine is selected from the group consisting of cetylamine and octylamine.

7. The method of claim 1, wherein said compound is at least one member selected from the group consisting of n-heptylamine, n-octylamine, decylamine, dodecylamine, hexadecylamine, octadecylamine, 2-aminooctene, naphythylamine, phenyl-n-propylamine, dephenylmethylamine, n-heptyl alcohol, n-octyl alcohol, dodecyl alcohol, hexadecyl alcohol, 1-octent-3-ol, naphthol, diphenylmethanol, 4-phenyl-2-butanol, glycidyl ethers of these alcohols, n-octanoic acid, nonanoic acid, 2-nonenoic acid, decanoic acid, dodecanoic acid, stearic acid, arachidonic acid, oleic acid, diphenylacetic acid, phenylpropionic acid, and halides, esters, and amides of these carboxylic acids, octyl chloride, octyl bromide, decyl chloride, dodecyl chloride, octanethiol, dodecanethiol, n-octyltrichlorosilane, octadecyltrichlorosilane, n-octylaldehyde, n-caprinaldehyde, and dodecylaldehyde.

8. The method of claim 1, wherein said water-soluble carrier is a cellulose gel.

9. The method of claim 1, wherein said value of log P is greater than 2.80.

10. The method of claim 1, wherein said value of log P is greater than 3.00.

11. The method of claim 1, wherein said water-soluble carrier has a value of contact angle with water of less than 60 degrees when the water-insoluble carrier is shaped into a flat plate.

12. The method of claim 1, wherein said body fluid is passed through a container packed with said absorbent, said container comprising an inlet for body fluid, and outlet for body fluid and filters for preventing said absorbent from flowing out of said inlet or outlet.

* * * * *